US007816327B2

(12) United States Patent
Manion

(10) Patent No.: US 7,816,327 B2
(45) Date of Patent: *Oct. 19, 2010

(54) INHIBITION OF ALLERGIC CONTACT DERMATITIS BY N-L-ALPHA-ASPARTYL-L-PHENYLALANINE 1-METHYL ESTER

(75) Inventor: Carl V Manion, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 69 days.

This patent is subject to a terminal disclaimer.

(21) Appl. No.: 11/861,231

(22) Filed: Sep. 25, 2007

(65) Prior Publication Data
US 2008/0227861 A1  Sep. 18, 2008

Related U.S. Application Data

(63) Continuation of application No. 11/106,201, filed on Apr. 14, 2005, now Pat. No. 7,288,527.

(60) Provisional application No. 60/566,034, filed on Apr. 27, 2004, provisional application No. 60/583,388, filed on Jun. 28, 2004.

(51) Int. Cl.
*C07K 5/06* (2006.01)
(52) U.S. Cl. ...................................................... 514/19
(58) Field of Classification Search .................... 514/19
See application file for complete search history.

(56) References Cited

U.S. PATENT DOCUMENTS

| | | | |
|---|---|---|---|
| 3,492,131 A | 1/1970 | Schlatter | |
| 4,259,318 A | 3/1981 | Duhe et al. | |
| 4,547,384 A | 10/1985 | Kryer | |
| 4,594,239 A | 6/1986 | Pluim, Jr. | |
| 4,663,151 A | 5/1987 | Waali | |
| 4,803,047 A | 2/1989 | Pluim, Jr. | |
| 4,861,584 A | 8/1989 | Powell, Jr. et al. | |
| 5,409,908 A | 4/1995 | Sanchez et al. | |
| 5,443,847 A | 8/1995 | West | |
| 5,602,183 A | 2/1997 | Martin et al. | |
| 5,643,572 A | 7/1997 | Byers et al. | |
| 5,654,334 A | 8/1997 | Edmundson et al. | |
| 5,747,052 A | 5/1998 | Mimikos et al. | |
| 5,767,109 A | 6/1998 | Sanchez et al. | |
| 5,998,473 A | 12/1999 | Edmundson et al. | |
| 6,156,795 A | 12/2000 | Edmundson et al. | |
| 6,177,467 B1 | 1/2001 | Edmundson et al. | |
| 6,326,400 B1 | 12/2001 | Edmundson et al. | |
| 6,384,076 B1 | 5/2002 | Manion et al. | |
| 6,436,429 B1 | 8/2002 | Peyman | |
| 6,630,191 B1 | 10/2003 | Amino et al. | |
| 6,919,374 B1 | 7/2005 | Manion et al. | |

FOREIGN PATENT DOCUMENTS

| | | |
|---|---|---|
| WO | WO 97/00692 | 1/1997 |
| WO | WO 98/13062 A1 | 4/1998 |
| WO | WO 00/18418 | 4/2000 |
| WO | WO 01/00153 A1 | 1/2001 |
| WO | WO 2004/039348 A1 | 5/2004 |
| WO | WO 2005/094776 A1 | 10/2005 |

OTHER PUBLICATIONS

Karlberg Ann-Therese (Chemical Research in Toxicology 21(1), 53-69, 2008).*
Szucs, et al.; The Effects of Aspartame on Mast Cells and Basophils, Fd. Chem. Toxic., 1986, pp. 171-174, vol. 24, No. 2, Great Britain.
Marks, et al. 1987 (Oral hyposensitization to poison ivy and poison oak, Arch Dermatol 123:476-478).
Epstein, W.L. 1989, "Topical prevention of poison ivy/oak dermatitis," Arch Dermatol 125:499-501.
Marks, et al. 1995, "Prevention of poison ovy and poison oak allergic contact dermatitis by quaternium-18 bentonite," J Am Acad Dermatol 33:212-216.
Gelber, et al. 1997, "Down-regulation of poison ivy/oak-induced contact sensitivity by treatment with a class II MHC binding peptide:hapten conjugate," J Immunol 158:2425-2434.
Baldwin, et al. 1999 "Regulation of the contact sensitivity response to urushiol with anti-urushiol monoclonial antibody ALG 991," Arch Dermatol Rews 291:652-658.
Vidmar, D.A. and Iwae, M.K. 1999 "Assessment of the ability of the topical skin protectant (TSP) to protect against contact dermatitis to urushiol (Rhus) antigen," Am J Contact Dermat 10:190-197.
Stibich, et al. 2000 "Cost-effective post-exposure prevention of poison ivy dermatitis," Int J Dermatol 39:515-518.
Couteau, et al.; Photodegredation Kinetics Under UV Light of Aspartame, 2000.
Manion, et al; Aspartame Effect in Sickle Cell Anemia, Clinical Pharmacology & Therapeutics, 2001, pp. 346-355, vol. 69. No. 5, United States.

* cited by examiner

*Primary Examiner*—David Lukton
(74) *Attorney, Agent, or Firm*—Eugenia S. Hansen; Hemingway & Hansen, LLP

(57) ABSTRACT

It has now been found that N-L-alpha-aspartyl-L-phenylalanine 1-methyl ester (APM) and/or one of its lower alkyl derivatives can be used to treat allergic contact dermatitis associated with irritating oils such as catechol-containing plant-derived antigens such as poison ivy, poison oak, poison sumac and Asian lacquer tree and oils containing capsaicin. Topical application of APM and/or derivative can reduce or alleviate the symptoms associated with irritation of the skin and/or mucous membranes caused by contact or inhalation of these oils or fumes from burning vegetation containing these oils.

7 Claims, No Drawings

INHIBITION OF ALLERGIC CONTACT DERMATITIS BY N-L-ALPHA-ASPARTYL-L-PHENYLALANINE 1-METHYL ESTER

CROSS-REFERENCE TO RELATED APPLICATIONS

This application is a continuation of U.S. application Ser. No. 11/106,201, filed Apr. 14, 2005, now U.S. Pat. No. 7,288,527, which claims the benefit of U.S. Provisional Application No. 60/566,034, filed Apr. 27, 2004 and U.S. Provisional Application No. 60/583,388, filed Jun. 28, 2004.

STATEMENT REGARDING FEDERALLY SPONSORED RESEARCH OR DEVELOPMENT

Not applicable.

REFERENCE TO A MICROFICHES APPENDIX

Not applicable.

TECHNICAL FIELD OF INVENTION

The present invention relates to the treatment of dermatitis caused by plant derived and other irritant substances with N-L-alpha-aspartyl-L-phenylalanine 1-methyl ester and/or derivatives.

BACKGROUND OF THE INVENTION

Irritant oils from members of the genus *Toxicodendron* and *Anacardiaceae*, which include but are not limited to poison ivy, poison oak, poison sumac, and the Asiatic lacquer tree can cause a dermatological allergic reaction marked by erythema, vesiculation, and severe pruritus. These oils, like oils from other plants such as the capsicum genus and oils of non-plant origin produce limited eruptions of allergic dermatitis in response to the presence of these oils. The dermatitis often corresponds to areas where plants or the irritant oils have touched the skin or by contact with objects such as clothing, shoes, toys, tools, or pets acting as carriers of the irritant oils from previous exposure to the plants or oils. Further, serious lung irritation can be caused by the spreading of the irritant oils in smoke from the burning or these plants or oils.

An example reaction that results from the main constituent of the irritant oils from poison ivy and related plants occurs from urushiol. Urushiol is a mixture of several compounds which are derivatives of catechol with unsaturated $C_{15}$ or $C_{17}$ side chains as shown below.

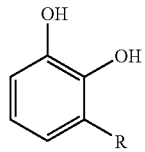

wherein R can be one of the following:
- I=—$(CH_2)_{14}CH_3$
- II=—$(CH_2)_7CH$=$CH(CH_2)_5CH_3$
- III=—$(CH_2)_7CH$=$CHCH_2CH$=$CH(CH_2)_2CH_3$
- IV=—$(CH_2)_7CH$=$CHCH_2CH$=$CHCH$=$CHCH_3$
- V=—$(CH_2)_7CH$=$CHCH_2CH$=$CHCH_2CH$=$CH_3$ The exact composition of urushiol differs for each plant. For example, urushiol from poison ivy (*T. radicans*) is a mixture catechol derivatives wherein R is defined by I, II, III and V given above. Urushiol for the Asiatic lacquer tree (*T. verniciferum*) is a mixture catechol derivatives wherein R is defined by of I, II, III and IV given above.

Within 10-15 minutes after contact, urushiol binds to skin proteins. Washing off urushiol with soap and water before binding occurs can generally prevent an allergic reaction. However, once bound, urushiol cannot be washed off or transferred to other areas. Attached to cell membranes, urushiol is presented to patrolling T-cells, thus initiating an allergen-specific immune response. Generally, within 12 to 48 hours, redness and swelling appears, followed by blisters and itching. The rash occurs only where urushiol has touched the skin; however, the rash may appear to spread if it appears over time instead of all at once. This is usually because either the urushiol is absorbed in different parts of the body at different rates or exposure to urushiol-contaminated objects is repeated over time.

Less irritant oils related to urushiol include those related to the capsicum genus of plants that produce methyl hydroxyl derivatives of catechol with unsaturated $C_{15}$ or $C_{17}$ side chains in the para rather than ortho position. The capsicum oils produce sensations of heat as well as irritation. Capsaicin is the active ingredient that alters and enhances the sense of taste that leads to its common use as a spice for food. Most of the catechol derived spicy oils, while irritating, are less biological sensitizing and do not prevent their dietary use or consumption.

Contact dermatitis caused by exposure to urushiol is generally treated symptomatically. Itching is commonly treated with wet compresses, oral antihistamines, and topical hydrocortisones. Prescription topical corticosteroids are prescribed in severe cases when treatment is begun within a few hours of exposure. Prescription oral corticosteroids are given in severe cases where the rash appears on the face, genitals, or covers more than 30% of the body. When irritant oils are ingested, there is no current preparation that can be commonly used to alter the ensuing course of events, including sensations of heat discomfort nor gastrointestinal discomfort. Numerous over-the-counter products are used to dry up the blisters: aluminum acetate, baking soda, aluminum hydroxide gel, calamine, kaolin, zinc acetate, zinc carbonate, and zinc oxide.

Research for therapeutic agents to protect against or disrupt the allergic response to urushiol and irritant oils has involved numerous approaches including desensitization, vaccines, and barrier creams. In one study, postexposure treatment with a surfactant (DIAL® dishwashing liquid, oil-removing compound (GOOP® Hand Cleaner) or a chemical inactivator (Oak-N-Ivy Brand TECNU® Outdoor Skin Cleanser) reportedly provided 56-70% protection when compared to positive control (Stibich, et al. 2000. "Cost-effective post-exposure prevention of poison ivy dermatitis," *Int J Dermatol* 39:515-518). Pre-exposure topical treatments and protectants have been reported: a topical lotion containing 5% quaternium-18 bentonite (Marks, et al. 1995. "Prevention of poison ivy and poison oak allergic contact dermatitis by quaternium-18 bentonite," *J Am Acad Dermatol* 33:212-216); organoclay (Epstein, W. L. 1989. "Topical prevention of poison ivy/oak dermatitis," *Arch Dermatol* 125:499-501); and topical skin protectant (TSP; ICD2289) (Vidmar, D. A. and Iwane, M. K. 1999. "Assessment of the ability of the topical skin protectant (TSP) to protect against contact dermatitis to urushiol (Rhus) antigen," *Am J Contact Dermat* 10:190-197). Downregulation of contact sensitivity to urushiol in mice has been attempted by systemic treatment with various substances: a monoclonal antibody to urushiol (Baldwin, et al. 1999. "Regulation of the contact sensitivity response to urushiol with anti-urushiol monoclonal antibody ALG 991," *Arch Dermatol Res* 291:652-658); and a synthetic I-Ak binding peptide coupled to 3-pentadecylcatechol (Gelber, et al. 1997. "Down-regulation of poison ivy/oak-induced contact sensitivity by treatment with a class II MHC binding peptide: hapten conjugate," *J Immunol* 158:2425-2434). In one study, a 1:1 mixture of pentadecylcatechol and heptadecylcatechol diacetate was administered to human subjects in an effort to reduce sensitivity to poison ivy and poison oak, but reportedly decreased sensitivity was not achieved (Marks, et al. 1987. "Oral hyposensitization to poison ivy and poison oak," *Arch Dermatol* 123:476-478).

U.S. Pat. No. 4,259,318 discloses use of the enzyme p-diphenol oxidase (laccase) as an effective topical treatment or prevention of poison ivy dermatitis.

U.S. Pat. No. 4,663,151 discloses use of aluminum chlorhydrate to prevent dermatitis caused by exposure to urushiol.

U.S. Pat. Nos. 4,803,047 and 4,594,239 disclose a method of neutralizing urushiol on surfaces with an aqueous solution comprising a water-soluble chlorine-containing compound.

U.S. Pat. No. 4,861,584 discloses a composition comprising an activated organophilic clay ion exchanged with a quaternary ammonium compound having aryl or alkyl groups in the range of 10-22 carbon atoms, and a vehicle comprising one or more long-chain hydrocarbons or volative silicon oils applied to the skin to block and absorb allergenic oils of toxic plants such as poison ivy.

U.S. Pat. No. 5,443,847 discloses a method for treating dermatitis caused by exposure to urushiol by topically applying a soluble manganese salt which acts as a chelating agent on urushiol, thus deactivating its toxicity.

U.S. Pat. No. 5,643,572 discloses compositions and methods of modulating immune responses to allergens such as urushiol using antibody molecules of either $Ab_1$ or $Ab_2$ reactivity to the sensitizing antigen.

U.S. Pat. Nos. 5,767,109 and 5,409,908 disclose use of cyclodextrins to complex urushiols to protect against and to treat irritation arising from exposure to urushiols.

U.S. Pat. No. 5,654,334 discloses N-L-aspartyl-L-phenyalanine 1-methyl ester (APM) and its derivatives as a pain reliever which is especially effective in relieving pain associated with osteoarthritis and multiple sclerosis. Further, International Application WO 97/00692 discloses APM as an antipyretic.

It has now been found that N-L-aspartyl-L-phenyalanine 1-methyl ester and its lower alkyl ester derivatives are effective in treating allergic dermatitis caused by exposure to plant-derived antigenic oils such as urushiol and that oral ingestion of N-L-aspartyl-L-phenyalanine 1-methyl ester also alters the duration, heat and irritation related to the intentional or accidental ingestion of spicy oils related to capsicum.

SUMMARY OF THE INVENTION

In one aspect, the invention is the use of the compound

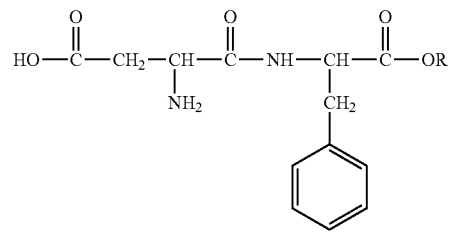

where R is H, $CH_3$ or an alkyl having 2-4 carbon atoms to prepare a pharmaceutical composition useful for treating allergic contact dermatitis resulting from exposure to urushiol and topical preparation in carriers preferably lotion or cream, saline solutions, and nebulizer solutions. A preferred compound has R=$CH_3$.

In another aspect, the invention is a method for treatment of allergic contact dermatitis in a patient resulting from exposure to urushiol by topical administration to the skin exposed to urushiol of an effective amount of a composition comprising the compound

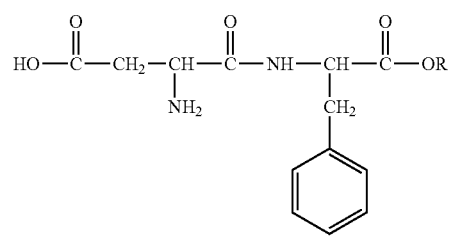

where R is H, $CH_3$ or an alkyl having 2-4 carbon atoms, wherein said treatment results in a reduction in the allergic immune response to urushiol. A preferred effective amount for topical administration of the compound is from about 0.1 to about 50 milligrams per ml of carrier. Most preferred is an effective amount of about 1.2 milligrams to about 12 milligrams per ml of carrier. A preferred compound has R=$CH_3$.

In another aspect, the invention is a method for treating allergic contact dermatitis resulting from exposure to urushiol comprising systemically administering an effective amount of a composition comprising the compound

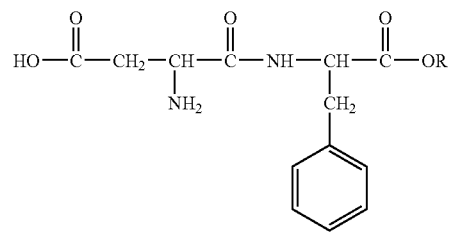

where R is H, $CH_3$ or an alkyl having 2-4 carbon atoms, wherein said effective amount causing a reduction in the allergic immune response to urushiol. A preferred effective amount for systemic administration is from about 1.0 to about 6 mg mg per kilogram of body weight. Most preferred is from about 1.5 milligrams to about 6 milligrams per kilogram body weight. A preferred compound has R=CH$_3$. A patient with allergic contact dermatitis can also be concomitantly treated systemically and topically with such compositions.

In another aspect, the invention is a method for preventing allergic contact dermatitis in a patient upon exposure to urushiol by prophylactically administering topically to skin which may be exposed to urushiol an effective amount of a composition comprising the compound

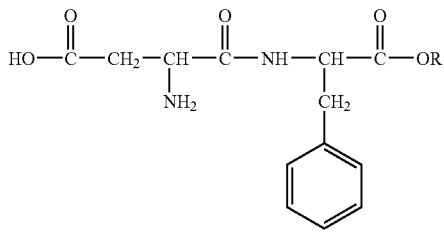

where R is H, CH$_3$ or an alkyl having 2-4 carbon atoms, wherein said treatment prevents an allergic immune response to urushiol. A preferred effective amount for prophylactic topical administration is from about 0.1 to about 50 milligrams per ml of carrier. Most preferred is from about 1.2 milligrams to about 12 milligrams per ml of carrier. A preferred compound has R=CH$_3$.

In another aspect, the invention is a method for decreasing sensations of heat and discomfort arising from oral ingestions of spicy oils like capsaicin or the accidental contact of pepper containing ingredients with sensitive mucosa, of eyes, mouth, or rectum by orally administering or topically applying an effective amount of a composition comprising the compound

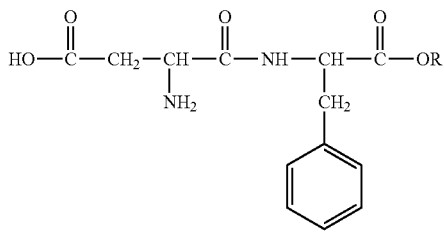

where R is H, CH$_3$ or an alkyl having 2-4 carbon atoms, wherein said treatment stops the burning irritation and restores normal sensitivity of the affected mucosa. A preferred effective amount for topical therapeutic administration is from about 0.1 to about 50 milligrams per ml of carrier. Most preferred is from about 1.2 milligrams to about 12 milligrams per ml of carrier. A preferred compound has R=CH$_3$.

DETAILED DESCRIPTION

It has now been found that N-L-alpha-aspartyl-L-phenylalanine 1-methyl ester (APM) can be used to effectively treat allergic contact dermatitis caused by catechol-containing allergens such as urushiol (hereinafter, catechol-containing allergens referred to as urushiol). Upon topical administration of an effective amount of APM, patients, having allergic dermatitis caused by exposure to urushiol, experience a reduction in symptoms. This may include a reduction in sensations of heat, pain, burning, swelling and itching. Time dependent symptoms of redness, swelling and blistering are altered or prevented by the early application of APM while delayed application impacts only the magnitude of events in progress (number of blisters, amount of redness, degree of swelling). Most results appear within minutes while well established dermatitis responses in progress from extended cellular mediator release may take hours to days to observe any definitive changes in the magnitude and extent of manifested pathologic alteration under observation, (e.g. swelling and blistering).

The variability in observable results in preventing dermatitis or topical irritation appear related to the amount of APM that is applied, the time and order of the therapeutic application, and the presence of receptors to which either the irritant oil or APM may bind. These events are demonstrated ideally in the common event of oral ingestion of capsaicin-containing spices like red pepper sauce, such as for example that sold under the brand name Tabasco® (McIlhenny Co. Avery Island, La.). The oral application of APM before red pepper sauce leads to an absence of recognition of the spicyness of said sauce. If a red pepper sauce is applied to the tongue first, and APM is applied after the developed sensations of heat and irritation occur, then displacement by APM of capsaicin from the taste receptor is manifested and recognized quickly. If a long duration of exposure to capsaicin is present leading to secondary effects, the APM response is not as strong nor as quick. This practical example demonstrates the limits and the general feature of an irritant oil binding to a pertinent receptor and how APM acts to effect the observed results.

In one aspect of the invention, APM is applied topically to a skin area affected by an irritating oil. A formulation of APM in a carrier suitable for topical application is preferred. Such a carrier may be, for example, a cream, gel, lotion, ointment, paste or liquid. Any amount of APM may provide a beneficial reduction in symptoms. A suitable formulation should contain from about 0.1 mg APM per ml of carrier to about 50 mg per ml of carrier. Preferably, a formulation effective for reducing symptoms of allergic contact dermatitis caused by an irritating oil is at least about 1 mg per ml of carrier. Most preferably, a quantity of APM from about 1.2 mg to about 12 mg per ml of carrier is employed in the formulation. The upper limit of APM utilized in the formulation is not critical since the objective is to provide a formulation which may contact the affected area and provide sufficient active ingredient to exert an effect. It is desirable to employ, therefore, the maximum amount of APM per ml so that the resulting formulation has the desired characteristics. In one instance, it may be desired that the APM used be soluble in the formulation, and in another, that the APM used be suspended in the formulation. In the latter instance, body fluid will solubilize the APM from the suspension during use so that the beneficial effects of APM can be realized. In one example, commercially available APM formulated as a powdered sweetener for beverages and foods may be used to formulate a topical preparation. APM powdered sweeteners typically contain about 36.7 mg APM per gram of powder, which may contain dextrose, maltodextrin and aspartame. One gram of powdered sweetener is normally provided in a commercial packet. The packets can be used to formulate a topical preparation by, for example, providing 1 to 8 packets of powdered sweetener per ounce (29.6 ml) of a lotion base. An effective topical APM preparation may be made by mixing a sufficient number of powdered sweetener packets, such as those sold under the brand name EQUAL® (Merisant Co., Monteno, Ill., USA) to a quantity of lotion until the resulting topical preparation has a gritty consistency, but still may be spread on the affected area. Such a preparation which utilizes a lotion base is estimated to contain from about 1.2 mg APM/ml (37 mg APM/fluid ounce) to about 10 mg APM/ml (296 mg APM/fluid ounce).

In a preferred embodiment, a topical formulation is prepared using purified APM in the range of about 0.1 to about 50 mg per ml of carrier. A purified APM is available from (SinoSweet Co., Ltd. (Yangzhu, Dapu Township, Yixing, Jiangsu 214226, China) and is characterized as an odorless, crystalline powder, which is chemically pure and contains no additives, preservatives, or colors.

The solubility of aspartame in water is dependent on pH and temperature, the maximum solubility is reached at pH 2.2 (20 mg/ml at 25° C.) and the minimum solubility at pH 5.2 pHi) is 13.5 mg/ml at 25° C. The stability of aspartame is dependent on time, temperature, pH and water activity. For use in some applications of the present invention, such as use in the eye, a solution may be desired at 25° C., pH 7.4. In order to achieve maximum solubility, of asparatame at this temperature and pH, one should dissolve APM or its derivative in a solvent such as sterile water or physiological saline. Preferably, the solution should be made up fresh since APM is more stable in the dry state. At a pH greater than 5, cyclisation with the formation of diketopiperazine reportedly occurs in APM solutions. Alternatively, a stable solution of APM at room temperature, pH 4.3 can be made and the pH adjusted to 7.4 just prior to use. In addition, a solution of APM at pH 7.4 can be made and frozen so that it can be thawed just prior to use. In order to sterilize a solution for which sterility may be desired (e.g. application to the eye) one may use a sterilizing technique that will not be harmful to the molecule. Since heat may degrade APM and its derivatives, one may use a sterilizing filter or other methods that will not harm the APM or derivative. It is acceptable to apply a solution which is saturated with APM and in which crystalline materials are present. Since the solution is not intended for IV use, the presence of crystalline material will identify its intended topical use. The absence of crystals would identify that the solution has reached the limits of its life because of solubility considerations.

In most topical applications, a pH of 7.4 is not necessary, and the character of the carrier may permit a wider pH range. Lotions may be made a mildly acidic pH conditions (e.g., pH 5-6) to aid in the stability and storage of the product and these are also suitable for use in the invention. A lotion with a low buffering capacity may be chosen and the pH neutralized on contact with the skin.

In a preferred method for making an APM solution for use at physiological pH, the APM is dissolved in sterile water and passed through a sterilizing filter, such as a HEPA (high efficiency particulate absorber) filter capable of excluding particulate matter one micron or larger, into a sterile container. The sterile container may be subjected to lyophilization, and the lyophilized APM stored until ready to use in a sealed, sterile container such as commonly used in the pharmaceutical industry. The lyophilized APM may be added to either a smaller or larger quantity of prepared sterile water or saline to either dissolve completely or to create a saturated solution. For example, a quantity of 250 mg APM can be added to a sufficient amount of sterile saline to achieve a concentration of 50 mg/ml, and in this case the solution will contain crystals. Alternatively, 250 mg APM can be dissolved in a larger volume of sterile saline. Using the lyophilized APM will avoid the pH and temperature degradation of APM at the desired pH 7.4 for use in the eye, mucous membranes, and lungs.

The methodology for making APM is known in the art, and APM is available commercially. Its preparation is disclosed in U.S. Pat. No. 3,492,131. It is believed that various modifications can be made to the APM molecule, and the resulting derivatives will also have utility in the claimed invention. Since the 1-methyl ester portion of the molecule is not believed to contribute to the therapeutic activity of the molecule, N-L-alpha-aspartyl-L-phenylalanine itself or other lower alkyl esters are believed to be effective. Other possible analgesic physiologically acceptable derivatives are believed to include N-acyl-L-(beta-substituted)-aspartyl-L-phenylalanine lower alkyl esters and N-acyl-L-(eta-substituted)-aspartyl-L-phenylalanine. Chemical modifications made to the APM molecule which do not reduce the physiologically active properties disclosed herein thus fall within the scope of this invention.

Application of the topical preparation may be repeated as often as desired for continued relief. In addition, a topical preparation may be applied prophylactically to the skin to guard against irritating oils. For example, a worker that commonly encounters poison ivy in his or her work may apply an APM topical formulation prior to commencing work each day.

For severe cases of allergic contact dermatitis, APM can be administered topically and concomitantly in a systemic oral, parenteral, intraperitoneal, or sublingual preparation, preferably at 1.5 milligrams to 6 milligram per kilogram body weight. It can be administered via ingestion of a food substance containing APM in a volume sufficient to achieve therapeutic levels. Alternatively, it can be enclosed in capsules, compressed into tablets, microencapsulated, entrapped in liposomes, in solution or suspension, alone or in combination with a substrate immobilizing material such as starch or poorly absorbable salts. Pharmaceutically compatible binding agents and/or adjuvant materials can be used as part of a composition. Tablets or capsules can contain any of the following ingredients, or compounds of similar nature: a binder such as microcrystalline cellulose, gum tragacanth or gelatin; an excipient such as starch or lactose; an integrating agent such as alginic acid; corn starch; a lubricant such as magnesium stearate; a glidant such as colloidal silicon dioxide; and additional sweetening and flavoring agents. When a capsule form is used, a liquid carrier such as a fatty oil may be used. Capsules and tablets can be coated with sugar, shellac and other enteric agents as is known. APM can also be in a controlled-release formulation.

With the exception of patients suffering from phenylketonuria, APM is considered as a GRAS (generally regarded as safe) substance. APM is commercially available, e.g., as ASPARTAME™ (G. D. Searle & Company, Chicago, Ill.). Its preparation is also disclosed in U.S. Pat. No. 3,492,131. While APM is preferred, it is believed that a derivative of APM which can interact with urushiol to disrupt the patient's allergic immune response to urushiol can also be administered as an effective treatment for allergic contact dermatitis. Exemplary derivatives include but are not limited to alkyl esters having 2-4 carbon atoms and the dipeptide. It is to be understood that "APM" used herein refers to N-L-alpha-aspartyl-L-phenylalanine 1-methyl ester or its derivative as defined above.

Example 1

Treatment of Allergic Contact Dermatitis

To an area of skin previously exposed to urushiol is applied a thin film of APM in a cream base. After sixty (60) minutes, the symptoms of allergic contact dermatitis are significantly reduced. Further treatment may include washing the affected area to remove and displace urushiol dissolved in the applied lotion and followed by reapplication of APM containing cream or lotion.

Example 2

Prevention of Urushiol-Induced Dermatitis on Human Skin

To an area of skin which may be exposed to urushiol is applied a thin film of APM suspended in a petroleum cream base. Symptoms of allergic contact dermatitis either do not appear or are significantly reduced.

Example 3

Treatment and Prevention of Urushiol-Induced Dermatitis on Human Skin

Patient 1 had a history of developing severe dermal reactions and rashes in the course of his usual occupation which involved the caring and raising of goats and maintenance of the fenced-in enclosure in which the goats were kept. The goats frequently consumed and were in contact with both poison sumac and poison ivy abundant in their enclosure without experiencing symptoms.

A topical APM preparation was made by mixing 2 to 3 packets of Equal® brand sweetener (80-120 mg of APM) with approximately 170 ml (5.5 fluid ounces) of lotion containing Vaseline® Intensive Care® Water Resistant Moisturizing Lotion (Unilever United States, Inc.), resulting in a lotion with 0.5 to 1 mg APM/ml. Patient 1 had previously used the lotion base without effect. Patient 1 also took two packets of Equal® brand sweetener by mouth in response to a symptom of diarrhea, a condition known to be associated with urushiol.

A soap and water scrub of the affected area was done one hour after application of the cream, and the affected area allowed to air dry.

Additional affected areas were then discovered on Patient 1, and a lotion was prepared for Patient 1 to use on these areas as well as unaffected areas that could come in contact with poison ivy during his work. Patient 1 used additional topical APM preparation approximately two to three times per day. An observation was made on the day after application that no rash or reaction had occurred.

Example 4

Treatment of Rash Caused by Urushiol

A human rash, with itching, in progress secondary to contact with an animal known to have had significant exposure to urushiol substances was arrested in 8 hours with 2 applications of aspartame in a Vaseline Intensive Care Lotion base (about 1.2 to 10 mg/ml). The itching ceased, and discomfort and irritation resolved within 8 hours. Overnight, the rash was gone, and the subject was found to be asymptomatic.

Example 5

Treatment of Lung Irritation Caused by Urushiol Exposure

A firefighter's lungs are exposed to volatilized urushiol oil upon encountering burning vegetation comprising poison ivy, poison sumac and other related plants, resulting in inflammation of the lung.

A pharmaceutical dosage form containing APM or a derivative thereof is administered orally to the firefighter at a dosage of 1.5 to 6 milligrams per kilogram body weight to prevent lung irritation. Alternatively, or in addition to taking APM orally, an inhalant mist containing APM or a derivative is administered before or after exposure to volatilized urushiol oil. On another occasion, when there is a likelihood that a fire could potentially release urushiol oil that could be breathed into the lungs, a firefighter may take a pharmaceutical mixture containing APM (orally or through inhaled or aspiration procedures) prior to exposure in order to prevent lung irritation caused by inhaled urushiol oil.

An inhalation solution may be prepared as a sterile solution containing about 20 to 250 mg of APM per ml of diluent, such as purified water or physiologic saline (0.9%) (the weight of APM per unit volume to be based on the assumed dosage for an average firefighter of approximately 80 kilograms in weight and the volume that may be delivered by the delivery system). The solution may be adjusted to the desired pH which will affect the maximum solubility of the APM. A preferred pH is 7.4. The inhalation solution can be stored in a small, air tight container and can be used in conjunction with a portable nebulizer. The solution can be delivered to the lungs by activation of the rubber bulb of the nebulizer to cause the inhalation solution to be converted to a mist by the mixing of air with the solution. The firefighter can put the mouthpiece of the nebulizer to his mouth and inhale deeply as the rubber bulb is pressed. The firefighter may repeat the inhalation until the volume inhaled will sufficiently contact the affected area or until the prescribed dosage is delivered. In the common practice of adding a quantity of solution containing a pharmaceutical substance to be delivered to a small quantity of saline (for example 5 ml) and requiring The subject to take in the whole of the resulting diluted pharmaceutical substance through a nebulizer, the preferred amount of APM delivered should be about 80 to about 120 mg. When preparing the solution to be nebulized, it should be noted that the amount received in a lung from any inhalation therapy is variable since the process involved in inhalation frequently is interrupted by coughing. When inhalation is momentarily interrupted by a cough the medicinal ingredients are usually swallowed, and the efficiency of delivery of inhaled medication may be about 50 to 60%. Therefore, the efficiency should be taken into account when preparing the solution to be nebulized.

The amount to treat an irritant in the lung can also be estimated on-site by the effect on the subject during administration. The effect of a contact irritant in the lung produces a cough, secretions, bronchospasm, and wheezing. The effect of the administered substance can be observed by noting the effect on these symptoms. Multiple treatments would be advantageous if the symptoms are not fully relieved, or are initially relieved but are observed to rebound. The increase in the ability to breathe and reduction in dyspnea signal that a sufficient amount has been provided to the subject.

Example 6

Treatment of Capsaicin Irritation with APM

A person eating spicy food seasoned with peppers is exposed to capsaicin, an irritant oil related to urushiol, causing an uncomfortable burning sensation on the tongue. APM or a derivative thereof is applied to the affected area as a dry powder in the amount of at least about 10 mg APM per 250 microliters of saliva, resulting in relief. Preferably, about 35 to about 80 mg of APM is applied to the area affected.

Example 7

Use to Alleviate Capsaicin Burning of the Eye

A kitchen worker is exposed to capsaicin oil from peppers during cooking preparation, the oil is transferred to his hands and then, by his hands, to his eyes, resulting in a burning sensation and pain. A pharmaceutical formulation containing APM or a derivative at about 10 mg per 250 microliters in sterile saline is applied to the affected eye and the burning sensation is alleviated. The application may be repeated in 15 min because tearing may dilute or wash away the active ingredients.

Example 8

Use of APM in Conjunction with Capsaicin's Medical Use

A patient is treated for arthritis with a capsaicin cream applied twice daily to the affected Joint. Capsaicin is absorbed by the transdermal tissue and then transported to joint area. After an appropriate interval, for instance 2-5 days, significant reduction in swelling, heat, redness, and pain is observed. However, the patient also inadvertently contacts his or her urethra, periurethra tissues, vaginal mucosa, rectal mucosa, eyes, or nose with the capsaicin cream, resulting in a sensation of burning and pain in the affected area. The patient immediately applies a pharmaceutical preparation comprising 38 mg of APM per 5 ml to the affected area, thus reducing or eliminating the burning and pain.

Example 9

Use of Derivatives of APM

Different substitutions to APM could markedly affect its sweetness. For instance, aspartame is 160-fold sweeter than sugar, while 20 different substituents to APM as disclosed in U.S. Pat. No. 6,630,191 have sweetening potency up to 10,000 times of sugar. In treating urushiol oil contact of oral mucosa and capsaicin burning of oral mucosa, it may be preferable to employ an APM with little or no sweetening activity, because the user may be unable to tolerate the intense sweetness which would be encountered with the use of aspartame or a derivative of even more concentrated sweetening potential. The 1-methyl ester group of the APM molecule is necessary for sweetness, but it may be substituted with no loss of efficacy in the present invention. Therefore, one of the following substances can be used in a topical application to treat the effects of urushiol or capsaicin oil on the skin or mucosa: N-L-alpha-aspartyl-L-phenylalanine itself or other lower alkyl esters thereof, N-acyl-L-(beta-substituted)-aspartyl-L-phenylalanine lower alkyl esters and N-acyl-L-(beta-substituted)-aspartyl-L-phenylalanine.

Example 10

Use of APM in Conjunction With other Skin Treatment Compositions

APM may be used as an ingredient for topical application in conjunction with other skin treatment compositions such as calamine lotion. APM may provide enhanced treatment of poison ivy and other skin conditions when employed in this manner.

I claim:

1. A method for treatment of contact dermatitis, comprising applying to the skin of a subject in need of such treatment a topical preparation comprising an amount of a compound of the formula:

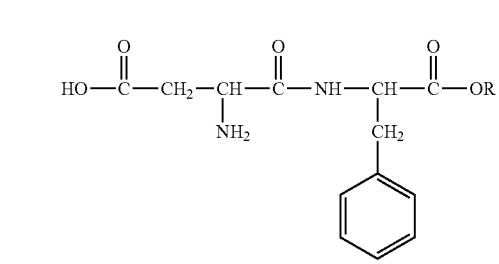

where R is H, $CH_3$ or an alkyl group having 2-4 carbon atoms, in combination with a carrier.

2. The method of claim 1, wherein R is an alkyl group having 2-4 carbon atoms.

3. The method of claim 2, wherein said amount is from about 0.1 to about 50 mg/ml carrier.

4. The method of claim 2, wherein said amount is from 1.2 mg/ml to about 12 mg/ml of carrier.

5. The method of claim 2, wherein said carrier is a lotion with a low buffering capacity.

6. The method of claim 2, wherein said alkyl group is ethyl.

7. The method of claim 6, wherein said carrier is a lotion.

* * * * *